(12) United States Patent
Hand et al.

(10) Patent No.: US 11,406,873 B2
(45) Date of Patent: Aug. 9, 2022

(54) TIMELINE AND MEDIA CONTROLLER FOR EXERCISE MACHINE

(71) Applicant: Tonal Systems, Inc., San Francisco, CA (US)

(72) Inventors: Michael Philip Hand, San Francisco, CA (US); Scott Matthew White, San Francisco, CA (US)

(73) Assignee: Tonal Systems, Inc., San Francisco, CA (US)

( * ) Notice: Subject to any disclaimer, the term of this patent is extended or adjusted under 35 U.S.C. 154(b) by 20 days.

(21) Appl. No.: 16/995,539

(22) Filed: Aug. 17, 2020

(65) Prior Publication Data

US 2021/0023417 A1 Jan. 28, 2021

Related U.S. Application Data

(63) Continuation-in-part of application No. 16/534,893, filed on Aug. 7, 2019, now Pat. No. 11,000,735.

(Continued)

(51) Int. Cl.
*A63B 24/00* (2006.01)

(52) U.S. Cl.
CPC ...... *A63B 24/0087* (2013.01); *A63B 24/0062* (2013.01)

(58) Field of Classification Search
CPC ............ A63B 24/0087; A63B 24/0059; A63B 24/0062; A63B 71/0622; A63B 23/03541; A63B 2220/808; A63B 2024/0093; A63B 2220/806; A63B 2071/0081; A63B 2220/836; A63B 2230/62; A63B 2071/0655; A63B 2230/062; A63B 2220/833; A63B 2230/436; A63B 2024/0068; A63B 2225/50; A63B 2071/0636; A63B 2071/0627; A63B 2071/0072; A63B 2071/065; A63B 2071/068; A63B 2230/40; A63B 2225/72; A63B 2071/0625; A63B 24/0075; A63B 2225/20; A63B 2220/807; A63B 71/0009; A63B 2071/063; A63B 2071/0638; A63B 2071/0666; A63B 2071/0675; A63B 2220/10; A63B 2220/17; A63B 2220/30; A63B 2220/40; A63B 2220/51; A63B 2220/54; A63B 2220/72; A63B 2220/73; A63B 2220/75; A63B 2220/80;

(Continued)

(56) References Cited

U.S. PATENT DOCUMENTS 5,474,083 A * 12/1995 Church ................. A61B 5/486
                                                             600/546
6,013,007 A *  1/2000 Root .................. A63B 24/0006
                                                             482/8

(Continued)

FOREIGN PATENT DOCUMENTS

WO      2013176933      11/2013

*Primary Examiner* — Garrett K Atkinson
(74) *Attorney, Agent, or Firm* — Van Pelt, Yi & James LLP

(57) ABSTRACT

A program is presented to a user including a stream of content including a first auditory content and a first visual content related to the workout. A context state of the user participating in the workout is determined based on information from a sensor. A responsive content is selectively added based on the context state of the user to the stream of content in a manner that avoids conflict with the stream of content.

27 Claims, 8 Drawing Sheets

Related U.S. Application Data

(60) Provisional application No. 62/716,861, filed on Aug. 9, 2018.

(58) Field of Classification Search
CPC ............ A63B 2230/06; A63B 2230/42; A63B 2230/50; G16H 20/30; G16H 50/20; G16H 40/63
See application file for complete search history.

(56) References Cited

U.S. PATENT DOCUMENTS

| | | | | |
|---|---|---|---|---|
| 6,347,290 | B1* | 2/2002 | Bartlett | G06F 1/1626 |
| | | | | 702/150 |
| 7,628,730 | B1* | 12/2009 | Watterson | A63B 22/02 |
| | | | | 482/8 |
| 7,789,800 | B1* | 9/2010 | Watterson | A63B 22/0023 |
| 8,029,415 | B2* | 10/2011 | Ashby | A63B 22/0605 |
| | | | | 482/49 |
| 8,827,870 | B2 | 9/2014 | Dyer | |
| 9,028,368 | B2* | 5/2015 | Ashby | A63B 23/0476 |
| | | | | 482/1 |
| 9,308,417 | B2* | 4/2016 | Grundy | A63B 21/4035 |
| 9,530,325 | B2* | 12/2016 | Hall | G09B 19/0092 |
| 10,052,518 | B2* | 8/2018 | Lagree | A63B 22/0087 |
| 10,311,462 | B2* | 6/2019 | Lindstrom, Jr. | G06Q 30/0241 |
| 10,839,954 | B2* | 11/2020 | Flavell | G16H 20/30 |
| 2001/0011025 | A1* | 8/2001 | Ohki | H04B 1/086 |
| | | | | 455/556.1 |
| 2004/0063551 | A1* | 4/2004 | Lightbody | A63B 21/00181 |
| | | | | 482/93 |
| 2004/0263473 | A1* | 12/2004 | Cho | G06F 3/0325 |
| | | | | 345/156 |
| 2006/0189439 | A1* | 8/2006 | Baudhuin | A63B 24/0075 |
| | | | | 482/8 |
| 2008/0051256 | A1* | 2/2008 | Ashby | A63B 23/12 |
| | | | | 482/5 |
| 2009/0270227 | A1* | 10/2009 | Ashby | A63B 22/0023 |
| | | | | 482/8 |
| 2011/0071003 | A1* | 3/2011 | Watterson | H04L 67/12 |
| | | | | 482/8 |
| 2011/0319229 | A1 | 12/2011 | Corbalis | |
| 2012/0196256 | A1 | 8/2012 | Maeueler | |
| 2012/0220427 | A1* | 8/2012 | Ashby | A63B 22/0605 |
| | | | | 482/4 |
| 2012/0323346 | A1* | 12/2012 | Ashby | A63B 22/0235 |
| | | | | 700/91 |
| 2013/0316316 | A1* | 11/2013 | Flavell | G16H 20/30 |
| | | | | 434/247 |
| 2014/0087341 | A1* | 3/2014 | Hall | G09B 5/02 |
| | | | | 434/258 |
| 2014/0278125 | A1* | 9/2014 | Balakrishnan | G16H 15/00 |
| | | | | 702/19 |
| 2014/0330186 | A1* | 11/2014 | Hyde | A61B 5/1118 |
| | | | | 602/19 |
| 2015/0238817 | A1* | 8/2015 | Watterson | A63B 23/0476 |
| | | | | 482/8 |
| 2016/0271452 | A1* | 9/2016 | Lagree | A63B 22/0076 |
| 2016/0346604 | A1* | 12/2016 | Lindstrom | G06F 16/68 |
| 2017/0007882 | A1 | 1/2017 | Werner | |
| 2017/0007884 | A1* | 1/2017 | Deutsch | A63B 71/03 |
| 2017/0065873 | A1* | 3/2017 | Hall | A63B 71/0622 |
| 2017/0172466 | A1* | 6/2017 | Eriksson | A61B 5/1112 |
| 2017/0266503 | A1* | 9/2017 | Watterson | A63B 22/0605 |
| 2017/0282015 | A1* | 10/2017 | Wicks | A63B 21/0058 |
| 2018/0154240 | A1* | 6/2018 | Hall | G09B 5/065 |
| 2019/0282857 | A1* | 9/2019 | Hapola | A63B 24/0062 |
| 2020/0047027 | A1* | 2/2020 | Ward | A63B 24/0021 |
| 2020/0047030 | A1* | 2/2020 | Ward | A61B 5/1128 |
| 2020/0047053 | A1* | 2/2020 | Ward | G06F 3/048 |
| 2020/0047054 | A1* | 2/2020 | Ward | G06F 3/0304 |
| 2020/0047055 | A1* | 2/2020 | Ward | A61B 5/1114 |
| 2020/0054929 | A1* | 2/2020 | Ward | G06F 3/017 |
| 2020/0254311 | A1 | 8/2020 | Watterson | |

* cited by examiner

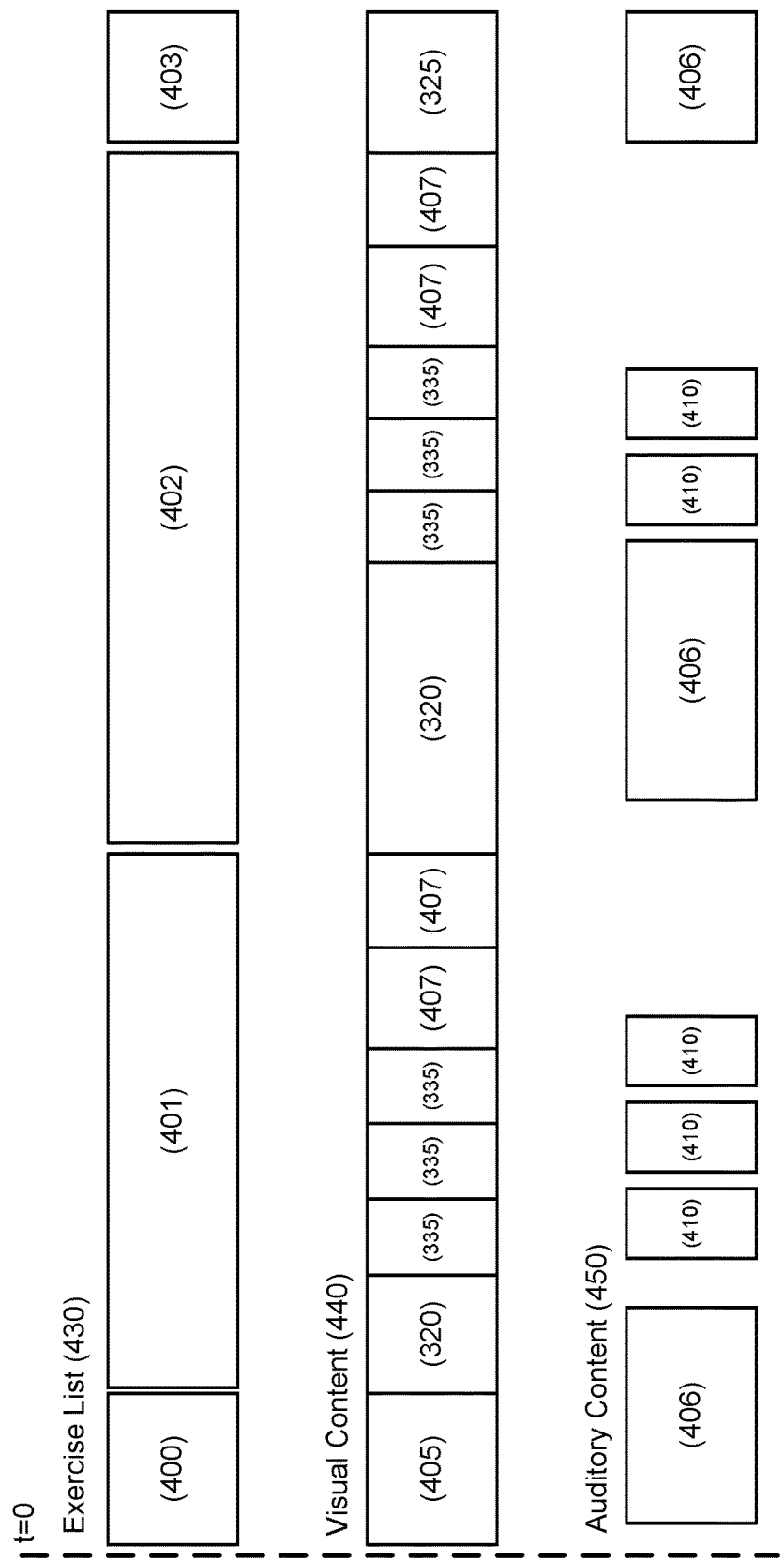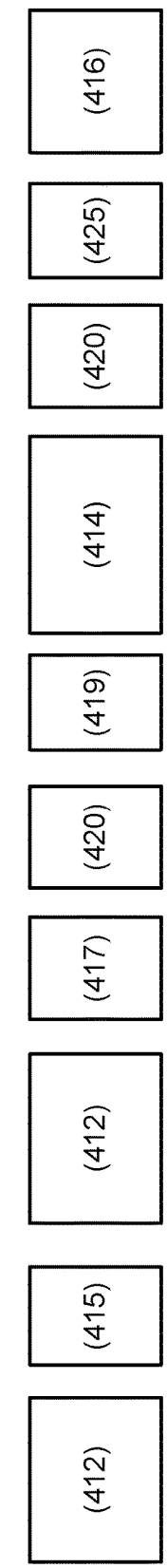
FIG. 4A
FIG. 4B

US 11,406,873 B2

TIMELINE AND MEDIA CONTROLLER FOR EXERCISE MACHINE

CROSS REFERENCE TO OTHER APPLICATIONS

This application is a continuation in part of pending U.S. patent application Ser. No. 16/534,893 entitled CONTROL SEQUENCE BASED EXERCISE MACHINE CONTROLLER filed Aug. 7, 2019, which claims priority to U.S. Provisional Patent Application No. 62/716,861 entitled VIDEO CENTERED MACHINE CONTROLLER filed Aug. 9, 2018 both of which are incorporated herein by reference for all purposes.

BACKGROUND OF THE INVENTION

Strength training requires repetition of a physical movement so that a user's muscle condition is enhanced by the repetitive loading. Typically a strength training exercise machine does not simulate an activity like running, biking, or rowing, but provides repetition of the abstract and/or isolated muscle loading movement.

Effective strength training programs that may not include an exercise machine include those where a user engages in a scheduled program at a gymnasium or fitness club under the tutelage of a coach. The coach may provide instruction, improvement, and/or encouragement of these repetitive movements, as repetition naturally leads to boredom and/or discouragement for many users. There is a need to provide the same instruction, improvement, and/or encouragement for users of strength training exercise machines.

BRIEF DESCRIPTION OF THE DRAWINGS

Various embodiments of the invention are disclosed in the following detailed description and the accompanying drawings.

FIG. 4A is a diagram illustrating an example of an exercise timeline in an embodiment of a system for controlling a workout, for example that shown in FIG. 2.

FIG. 4B is a diagram illustrating an example of an auditory clip.

DETAILED DESCRIPTION

Figure 1:
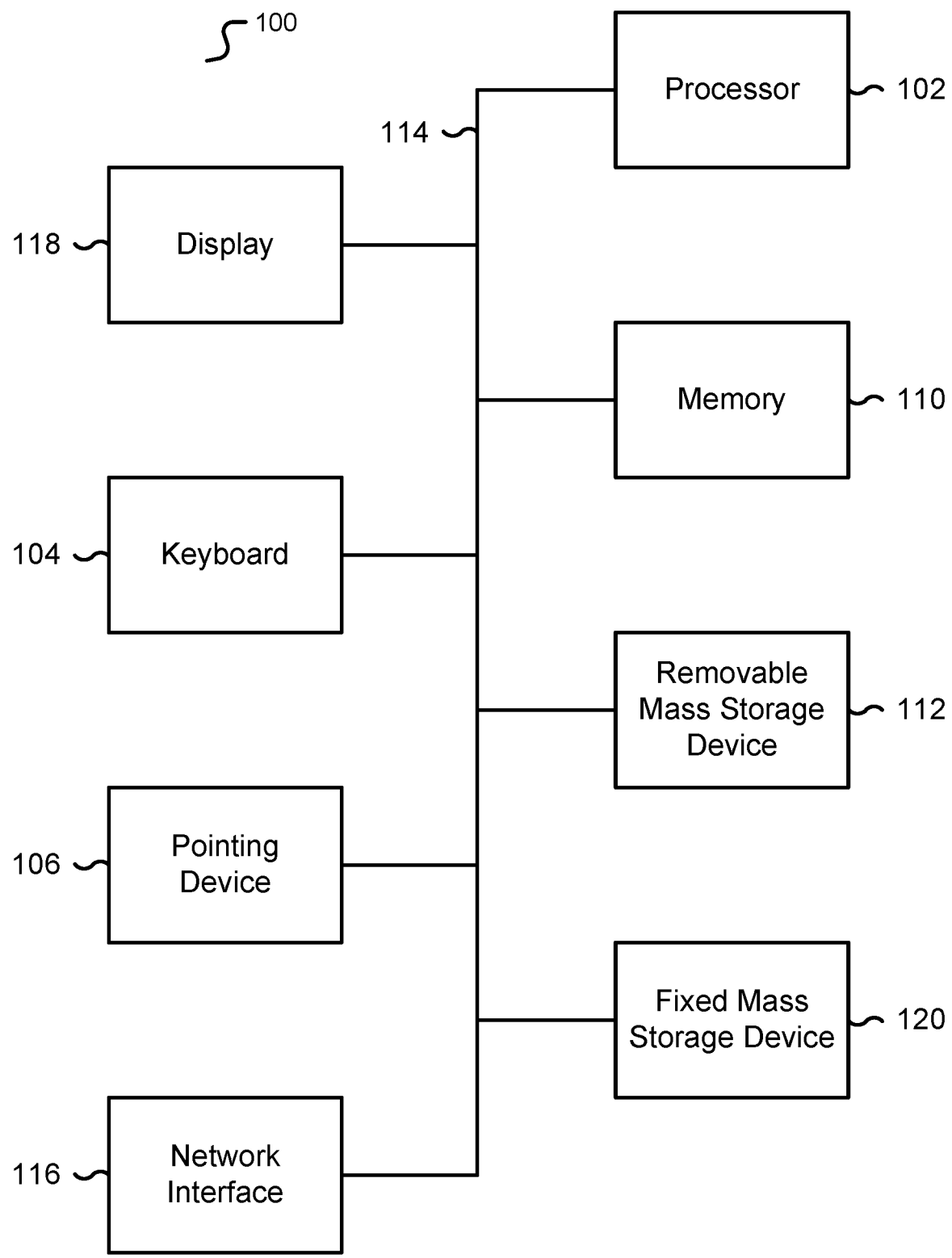
FIG. 1 is a functional diagram illustrating a programmed computer/server system for timeline and/or media control for an exercise machine in accordance with some embodiments.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Dynamically creating and/or editing a media timeline for a strength training exercise machine user is disclosed. The media timeline is presented in video, audio, and/or text or icon form to the user as they exercise using the strength training machine. In one embodiment, the media timeline is planned statically based on an initial context state of a user including a selection of a workout and a past history of workouts.

As more context information on how the user is doing for the current workout is sensed, responsive content is dynamically generated and appropriately preempts the existing media timeline, for example gracefully interrupting a coached workout including a general discussion from a coach with a verbal encouragement from the coach that "Hey Joe, I see you are struggling on your bench press, breathe through these last three reps; we will get to those gobble squats!" and/or an appropriate adjustment to video to present a seamless coaching media clip to the user, and/or reinforced by a text or icon message on an exercise machine display.

Such an encouragement requires user context including: the user name "Joe"; a state of a user as "struggling" to flag for encouragement; a mood selection for the user indicating they respond best to an "upbeat" message rather than for example a fierce message; a state of a user indicating this type of encouragement has not been done recently and may not seem repetitive; current exercise as "bench press"; the number of repetitions left of a set as "three"; and/or a future state of the next exercise being "gobble squats".

Providing instruction and/or information to a user engaged in strength and endurance training is disclosed. This includes services normally provided by an in-person personal coach including monitoring the performance of a user, identifying problems as they are detected, and providing encouragement to support the user.

FIG. 1 is a functional diagram illustrating a programmed computer/server system for timeline and/or media control for an exercise machine in accordance with some embodiments. As shown, FIG. 1 provides a functional diagram of a general purpose computer system programmed to provide timeline and/or media control for an exercise machine in accordance with some embodiments. As will be apparent, other computer system architectures and configurations may be used for timeline and/or media control for an exercise machine.

Computer system 100, which includes various subsystems as described below, includes at least one microprocessor subsystem, also referred to as a processor or a central processing unit ("CPU") (102). For example, processor (102) can be implemented by a single-chip processor or by multiple cores and/or processors. In some embodiments, processor (102) is a general purpose digital processor that controls the operation of the computer system 100. Using instructions retrieved from memory (110), the processor (102) controls the reception and manipulation of input data, and the output and display of data on output devices, for example display and graphics processing unit (GPU) (118).

Processor (102) is coupled bi-directionally with memory (110), which can include a first primary storage, typically a random-access memory ("RAM"), and a second primary storage area, typically a read-only memory ("ROM"). As is well known in the art, primary storage can be used as a general storage area and as scratch-pad memory, and can also be used to store input data and processed data. Primary storage can also store programming instructions and data, in the form of data objects and text objects, in addition to other data and instructions for processes operating on processor (102). Also as well known in the art, primary storage typically includes basic operating instructions, program code, data, and objects used by the processor (102) to perform its functions, for example programmed instructions. For example, primary storage devices (110) can include any suitable computer-readable storage media, described below, depending on whether, for example, data access needs to be bi-directional or uni-directional. For example, processor (102) can also directly and very rapidly retrieve and store frequently needed data in a cache memory, not shown. The processor (102) may also include a coprocessor (not shown) as a supplemental processing component to aid the processor and/or memory (110).

A removable mass storage device (112) provides additional data storage capacity for the computer system 100, and is coupled either bi-directionally (read/write) or uni-directionally (read only) to processor (102). For example, storage (112) can also include computer-readable media such as flash memory, portable mass storage devices, holographic storage devices, magnetic devices, magneto-optical devices, optical devices, and other storage devices. A fixed mass storage (120) can also, for example, provide additional data storage capacity. One example of mass storage (120) is an eMMC or microSD device. In one embodiment, mass storage (120) is a solid-state drive connected by a bus (114).

Mass storage (112), (120) generally store additional programming instructions, data, and the like that typically are not in active use by the processor (102). It will be appreciated that the information retained within mass storage (112), (120) can be incorporated, if needed, in standard fashion as part of primary storage (110), for example RAM, as virtual memory.

In addition to providing processor (102) access to storage subsystems, bus (114) can be used to provide access to other subsystems and devices as well. As shown, these can include a display monitor (118), a communication interface (116), a touch (or physical) keyboard (104), and one or more auxiliary input/output devices (106) including an audio interface, a sound card, microphone, audio port, audio recording device, audio card, speakers, a touch (or pointing) device, and/or other subsystems as needed. Besides a touch screen and/or capacitive touch interface, the auxiliary device (106) can be a mouse, stylus, track ball, or tablet, and is useful for interacting with a graphical user interface.

The communication interface (116) allows processor (102) to be coupled to another computer, computer network, or telecommunications network using a network connection as shown. For example, through the communication interface (116), the processor (102) can receive information, for example data objects or program instructions, from another network, or output information to another network in the course of performing method/process steps. Information, often represented as a sequence of instructions to be executed on a processor, can be received from and outputted to another network. An interface card or similar device and appropriate software implemented by, for example executed/performed on, processor (102) can be used to connect the computer system 100 to an external network and transfer data according to standard protocols. For example, various process embodiments disclosed herein can be executed on processor (102), or can be performed across a network such as the Internet, intranet networks, or local area networks, in conjunction with a remote processor that shares a portion of the processing. Throughout this specification "network" refers to any interconnection between computer components including the Internet, Bluetooth, WiFi, 3G, 4G, 4GLTE, GSM, Ethernet, TCP/IP, intranet, local-area network ("LAN"), home-area network ("HAN"), serial connection, parallel connection, wide-area network ("WAN"), Fibre Channel, PCI/PCI-X, AGP, VLbus, PCI Express, Expresscard, Infiniband, ACCESS.bus, Wireless LAN, HomePNA, Optical Fibre, G.hn, infrared network, satellite network, microwave network, cellular network, virtual private network ("VPN"), Universal Serial Bus ("USB"), FireWire, Serial ATA, 1-Wire, UNI/O, or any form of connecting homogenous, heterogeneous systems and/or groups of systems together. Additional mass storage devices, not shown, can also be connected to processor (102) through communication interface (116).

An auxiliary I/O device interface, not shown, can be used in conjunction with computer system 100. The auxiliary I/O device interface can include general and customized interfaces that allow the processor (102) to send and, more typically, receive data from other devices such as microphones, touch-sensitive displays, transducer card readers, tape readers, voice or handwriting recognizers, biometrics readers, cameras, portable mass storage devices, and other computers.

In addition, various embodiments disclosed herein further relate to computer storage products with a computer readable medium that includes program code for performing various computer-implemented operations. The computer-readable medium is any data storage device that can store data which can thereafter be read by a computer system. Examples of computer-readable media include, but are not limited to, all the media mentioned above: flash media such as NAND flash, eMMC, SD, compact flash; magnetic media such as hard disks, floppy disks, and magnetic tape; optical media such as CD-ROM disks; magneto-optical media such as optical disks; and specially configured hardware devices such as application-specific integrated circuits ("ASIC"s), programmable logic devices ("PLD"s), and ROM and RAM devices. Examples of program code include both machine code, as produced, for example, by a compiler, or files containing higher level code, for example a script, that can be executed using an interpreter.

The computer/server system shown in FIG. 1 is but an example of a computer system suitable for use with the various embodiments disclosed herein. Other computer systems suitable for such use can include additional or fewer subsystems. In addition, bus (114) is illustrative of any interconnection scheme serving to link the subsystems. Other computer architectures having different configurations of subsystems may also be utilized.

Figure 2:
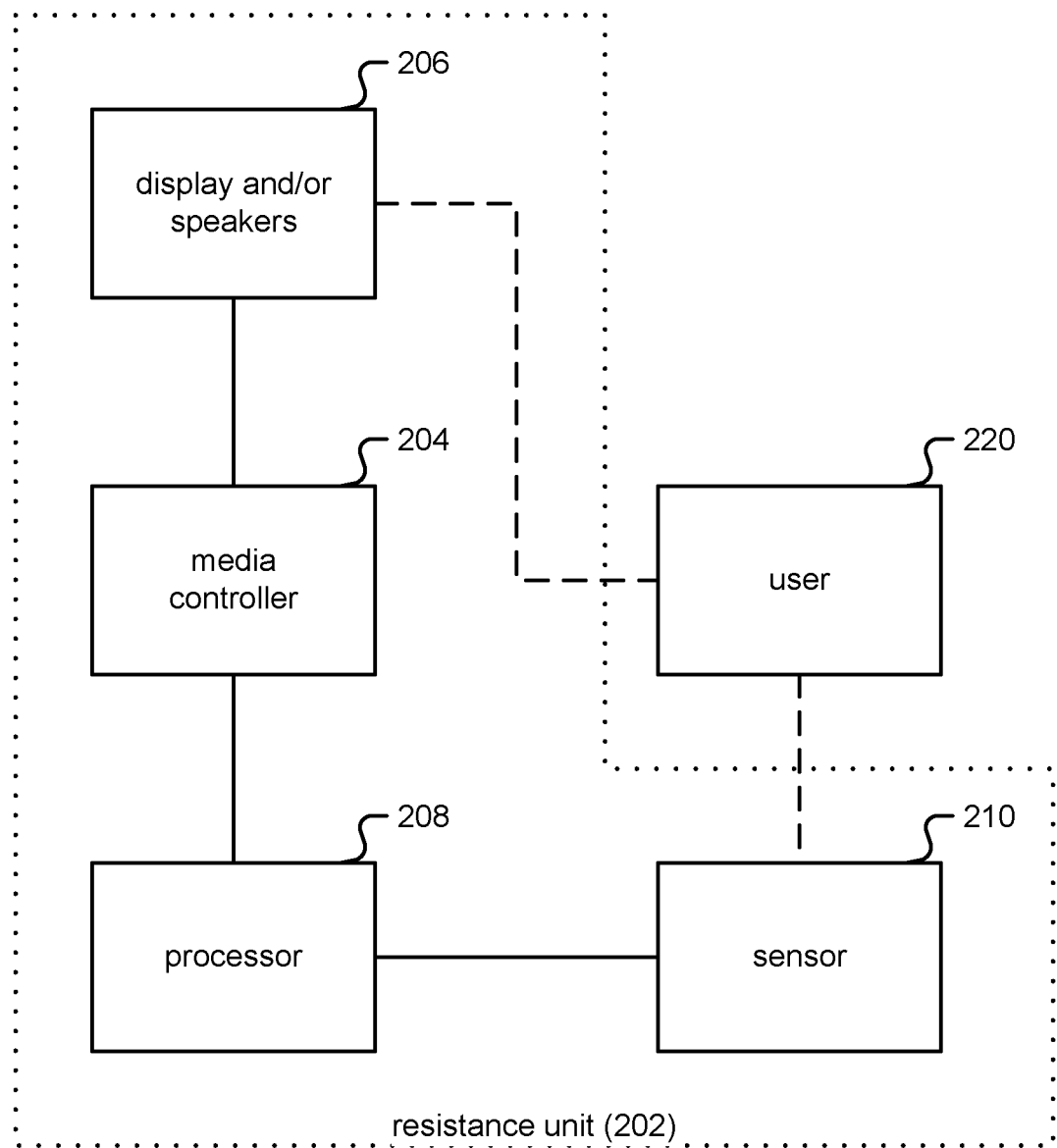
FIG. 2 is a block diagram illustrating an embodiment of a system for timeline and/or media control.

FIG. 2 is a block diagram illustrating an embodiment of a system for timeline and/or media control. In one embodiment, within the exercise machine (202) itself that provides resistance to motion against which the user (220) exercises, the system includes: a media controller (204) including a memory which comprises exercise machine control information and storage comprising video, audio, and text or icon content as well as sequencing instructions; a display/speakers (206) needed to present media to the user; a central processor (208); and a sensor (210) to provide user context. With this system, user performance may be tracked throughout the exercise period and user data accumulated and stored.

Sensor (210) as referred to herein includes: a power switch, a database query result, a clock, a calendar, a touch screen, a button or touch based control interface, a remote button or touch based controller, a camera, a microphone, a depth sensing camera, a seat sensor, a push force sensor for a user foot, a pull force sensor for a user foot, a seat to rail position sensor, a handle position sensor, a handle orientation sensor, a handle button(s), a cable position, speed, acceleration sensor, a cable tension sensor, a torque sensor, a current sensor(s), a voltage sensor(s), a wearable sensor such as a watch or belt to pick up on biometrics such a heart rate sensor, pulse-ox, respiration, position.

This data may be analyzed and compared with other available information which allow user exercise to be compared and optimized for better results. Workouts comprising sets of repetitions (or "reps") may be planned and then analyzed on the fly as a user proceeds. A user's progress may provide user context and media may be dynamically altered to modify a simulated coaching to best encourage or improve a user.

Context as referred to herein includes: personalized identifier, user name, user age, user sex, user height, user weight, user health history, user workout history, user heart rate, user respiration rate, user VO2 max, user oxygen saturation, user body temperature, user activity tracking, user fitness tracking, user sleep tracking, user mood, user coaching style preference, user preferences, environmental temperature, environmental humidity, location, altitude, workout, movement, set number, rep number, user performance for current and historical/past reps, user plan for future reps, historical/past and current coaching content, exercise machine physical configuration, exercise machine status, and/or whether the exercise machine is in an emergency stop.

In one embodiment, the exercise appliance (202) passes a load/resistance against the user via one or more lines/cables, to a grip(s) that a user displaces to exercise. A grip may be positioned relative to the user using a load arm and the load path to the user may be steered using pulleys at the load arm ends. The load arm may be connected to the exercise appliance frame using a carriage that moves within a track that may be affixed to the main part of the frame. In one embodiment, the frame is firmly attached to a rigid structure such as a wall.

In one embodiment, the appliance (202) includes a controller (204) and/or processor (208), which monitor/measure user performance, for example using one or more sensors (210), and determine loads to be applied to the user's efforts in the resistance unit (202). Without limitation, the media controller (204) and processor (208) may be separate control units or combined in a single package. The controller (204) is further coupled to a display/acoustic channel (206) that allows instructional information to be presented to a user (220) and with which the user (220) interacts in a visual manner, referred to herein as any method of communication based on the eye such as video and/or text or icons, and/or an auditory manner, referred to herein as any method of communication based on the ear such as verbal speech, text-to-speech synthesis, and/or music. Collocated with an information channel is a data channel that passes control program information to the processor (208) which then generates the exercise loading schedules. The display (206) may be incorporated into the exercise machine. In one embodiment, the display (204) is a large format, surround screen representing a virtual reality/alternate reality environment to the user; a virtual reality and/or alternate reality presentation may also be made using a headset (206).

In one embodiment, the appliance controller (204) provides audio information that is related to the visual information from a program store/repository that may be coupled to external devices or transducers (206) to provide the user with an auditory experience that matches the visual experience. Control instructions that set the operational parameters of the resistance unit (202) for controlling the load or resistance for the user may be embedded with the user information so that the media package includes everything needed for the controller to run the machine. In this way a user (220) may choose an exercise regime and may be provided with cues, visual and auditory as appropriate, that allow the actions of a personal trainer to be emulated. The controller may further emulate the actions of a trainer using an expert system and thus exhibit artificial intelligence. The user may better form a relationship with the emulated coach or trainer, and this relationship may be encouraged by using emotional/mood cues whose effect may be quantified based on performance metrics gleaned from exercise records that track user performance in a feedback loop using, for example, the sensor(s) (210).

The appliance controller may also be coupled to the environmental control for the exercise area so that exercise parameters may be optimized, adjusting lighting, temperature and humidity as appropriate based on telemetry such as home automation telemetry via an API, and/or sensors (210). The controller (204) and/or processor (208) may also be responsive to the environmental conditions prevailing so that the exercise routines may be moderated to stay within reasonable performance expectations; for example if the humidity is high, a lower rate of working may be requested from the appliance either under automatic control by the controller logic, or at the user's request. The appliance (202) may be entirely self-contained and/or connected to a data service that allows the appliance's exercise program or programs and operational parameters to be changed.

The appliance controller (204) determines and schedules not only the operation of the exercise appliance, but also the actions of one or more coaches who appears to the user (220). The coach may be a virtual coach, an abstraction such as an animation or other drawn art coach, and/or a live coach. The load or resistance applied, against which a user exercises, is determined by the processor (208) and may be provided by one or more actuators, such as an electric motor which facilitates a wide range of exercise parameters. Sensor(s) (210) measure user action and this information may be processed by the controller (204) and processor) to be used interactively with exercise parameters.

As an improvement over traditional techniques with static visual/auditory run on an exercise machine, such an appliance (202) may personalize coaching for a user (220) and/or to otherwise improve encouragement for the user (220) to continue with an exercise regime provided by the exercise machine, which are physically beneficial to the user and/or may be otherwise more boring. Because the controller is able to determine the user status at any time during exercise, exercise conditions may be adapted dynamically and the actions of the trainer/coach may be adjusted in near-real time to reflect changes, which improves user encouragement and/or trust in the exercise machine.

The user may also be able to influence the exercise routine directly by requesting a change. This process may be a dynamic process and not statically predetermined prior to beginning the exercise routine. For example, the exercise tempo may be altered, the number of repetitions may be adjusted, the workload may be altered, and the user may request these changes at any time prior to the end of the exercise segment where an exercise terminates. The exercise machine may dynamically adjust the media content to reflect user requests in a manner that avoids significant discontinuity/interruption, gracefully simulating the actions of a coach including requests, such as asking the user if they wish to extend or alter the exercise segment or routine.

Figure 3:
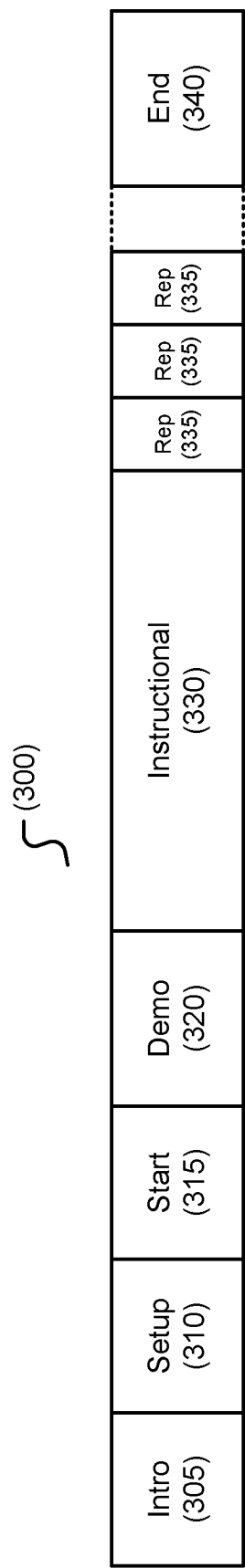
FIG. 3 is a diagram illustrating an example of an exercise sequence in an embodiment of a system for controlling a workout, for example that shown in FIG. 2.

FIG. 3 is a diagram illustrating an example of an exercise sequence in an embodiment of a system for controlling a workout, for example that shown in FIG. 2.

The exercise sequence (300) in FIG. 3 is displayed as event sequences in time starting at the left of FIG. 3. In this example, the sequence (300) is divided into events. Each event is represented in FIG. 3 by duration in the horizontal axis and lies adjacent to its prior and subsequent events. Without limitation, no relative scale is implied by the illustration of FIG. 3.

The first event (305) may be an introduction with a welcome message along with some guidance about how to interact with the system in FIG. 2. There may be visual and/or auditory content, and/or operational programming for the system. The next event (310) may be an initialization or setup routine; in this case, unless there are user directions, visual/auditory content may be absent. If there are user directions, such as swapping grips to the system, then the appropriate guidance content may be offered.

The next event (315) may start a workout. This may be a simple start up that starts the resistance load against the user and may be of short duration. The next event (320) may be a visual demonstration shown to the user coupled with auditory content before an instructional event (330) is started. Typically this instructional element (330) is interactive, with the user performing exercise at the system alongside the system visual and auditory content. Once an instructional element (330) is complete, then a user encounters a series of repetition elements (335) which are initially predefined based on the user's level of performance. The conclusion of the last repetition element lead to the end of the workout (340).

FIG. 4A is a diagram illustrating an example of an exercise timeline in an embodiment of a system for controlling a workout, for example that shown in FIG. 2. In one embodiment, the exercise timeline comprises concatenated exercise sequences (300) from FIG. 3. Time progresses from zero at the left edge of FIG. 4A.

Each horizontal region in FIG. 4A represents one of an exercise list (430), visual content (440), or auditory content (450). For ease of illustration, visual content (440) is shown as something on the user display (206) of FIG. 2 at any time when the user is present including fades and black-out clips, but the auditory content (450) is shown in FIG. 4A when instructional or commentary content is present wherein music track or background noise is not shown. In one embodiment, introduction (400) is accompanied by a visual segment (405) and, a short time after the beginning, auditory segment (406) is activated.

At the end of the introduction (400), the first exercise element (401), for example a goblet squat movement, starts with an instructional visual element (320) which the auditory segment (406) flows on from the introduction. As the user progresses in their exercise, reps (335) are available as visual content and the auditory component (410) that is relevant to the repetitions for this particular exercise occurs so as to supplement the visual stimulus. For example, the auditory content in FIG. 4A overlaps breaks in the actual exercise effort by the user but offers continuity in terms of encouragement/motivation to the user.

After the reps (335) have been completed, and the user cools down, video information (407) may still be present. For example, if a background of a group exercise is being used then, as the coach is deprecated in the display, the ending workouts of others may be shown to ease continuity and to show posture or a gradual reduction in work.

During this changeover period, the next programming information may be loaded to the appliance controller (204) in FIG. 2. This is the new exercise element (402), for example a bench press movement, and the instruction visual element (320) begins, accompanied by auditory information (406). Once again, as reps are being worked, auditory information (410) may be provided, and is typically different in content to that in the prior exercise (401). As shown in FIG. 4A, this is the end of the exercise (403), so the video content (325) is different from a normal introduction and the concluding matching audio (406) is different as well.

The exercise machine of FIG. 2 may treat the timeline of FIG. 4A ultimately as a single virtual file for display (206) of FIG. 2, comprised of segments and clips along with matching information for the speakers (206) of FIG. 2. In this way the resources required by the hardware are reduced and/or kept to a minimum. Generally, visual information (440) is continuous whereas auditory information (450) is relatively sparse, although if background music and/or sounds are desired, this may be mixed in and added.

By separating auditory and visual parts, alternative/supplementary clips may be incorporated. For example, to avoid boredom from any repetitive nature of the coaching audio, it may be desirable to intersperse "small talk" as commentary. When the auditory stream (450) is sparse, there may be an opportunity to fill in the silence with topical items without distraction, which may improve verisimilitude to coaching and reduce impersonal content. There may be emotional or other hazards implicit in arbitrary supplementation and one improvement is reducing this category of content to lighter/trivial matters, avoiding weighty topics that may cause offense/distraction.

As shown in FIG. 4A, a timeline is constructed so as to present a user with appropriately synchronized information in terms of both meeting the need of having lifelike auditory and visual coaching, and so that the coaching accurately matches the exercise itself. Because the exercise machine in FIG. 2 measures the user's performance continually during an exercise, this information may be used to make fine adjustments to tempo and effort without losing continuity. Because information storage is relatively inexpensive, versions of visual information having slightly different timing for aspects of the exercise may be substituted, whereas auditory information may be supplemented by altering the duration of, or filling, the silent space that lies between auditory elements.

FIG. 4B is a diagram illustrating an example of an auditory clip. The auditory segment (406), also shown in FIG. 4A, comprises utterances that are interspersed with nominally discrete silent periods; the matter of silent periods which result from unvoiced particles of speech is not represented for clarity herein. Utterances (412) are separated by a silent period (415) as might be found when a coach instructs a user to "pull . . . pull" synchronized with the effort to work against a load simulating say a rowing action. The cadence of the "pull . . . pull . . . pull" may exceed the user's working capacity, whether from basic capability or as a result of tiredness and so, in FIG. 2B the silent period (415) may need to be extended to accommodate the reduced user cadence over the workout. However, simply extending the space (415) may be discouraging for a user because the change in tempo that is perceived by the user may be emphasized as a negative response.

An improvement is to extend the effective silent period by inserting a filler word (420) while altering the duration of the silent periods (417) and (419) that now separate the filler utterance (420) from the utterances (412) and (414) respectively to achieve the total delay needed to create the reduced cadence. For example the filler word might be "and" so that the new combined utterance would be "pull . . . and . . . pull" and the time between the instructions to "pull" is now lengthened. In the case where an even longer extension to the cadence is required, a second filler utterance (425) may be inserted after the first filler utterance (420).

When altering silent periods to achieve a total desired cadence timing, the choice of filler words is made with the provision that an utterance should sound reasonably natural and not forced, since rapid speech would otherwise cue impatience, which may reduce the user's enthusiasm. The use of tones as filler utterances is also possible, but because this is not a normal part of speech it may prove irritating to a majority of users and is not generally used other than as a countdown cue, where the precursor to a long "start" tone is a series of shorter tones similar to that found in time reference broadcasts.

Data Structure. In order to support a timeline as shown in FIG. 4A, media clips may be organized using tags or any metadata without limitation that allow on-the-fly editing of the visual/auditory content at the client/exercise machine, for example for auditory content:

TABLE 1

Example Tags/Metadata for Content

| Tag | Description |
| --- | --- |
| coach | flag on for content where coach is speaking |
| encouragement | flag on for content with encouraging coaching |
| constructive | flag on for content with constructive coaching |
| upbeat | flag on for content with upbeat coaching |
| downbeat | flag on for content with downbeat coaching |
| fierce | flag on for content with fierce coaching |
| gentle | flag on for content with gentle coaching |
| movement | list of which movement(s) content is associated with, for example {"bench press", "angled bench press"} |
| side | enumerated values for content being associated with a "left" side, "right" side, "either", or "both" sides in relation to a movement. |
| weightOn | flag on for content appropriate when weight/resistance is actively exerted on user. |
| lastMinutes | value/range of how many last minutes of a movement the content is associated with, for example a clip may be appropriate for the last value = 5 minutes of a movement. |
| prescribedReps | value/range of how many prescribed reps of a movement the content is associated with, for example a clip may be appropriate for the rep number range = [1 thru 10] of a movement |
| lastPlayed | value/range of when the clip was last played, for example a clip may have been played last at value = 15:08 UTC. |

Figure 5A:
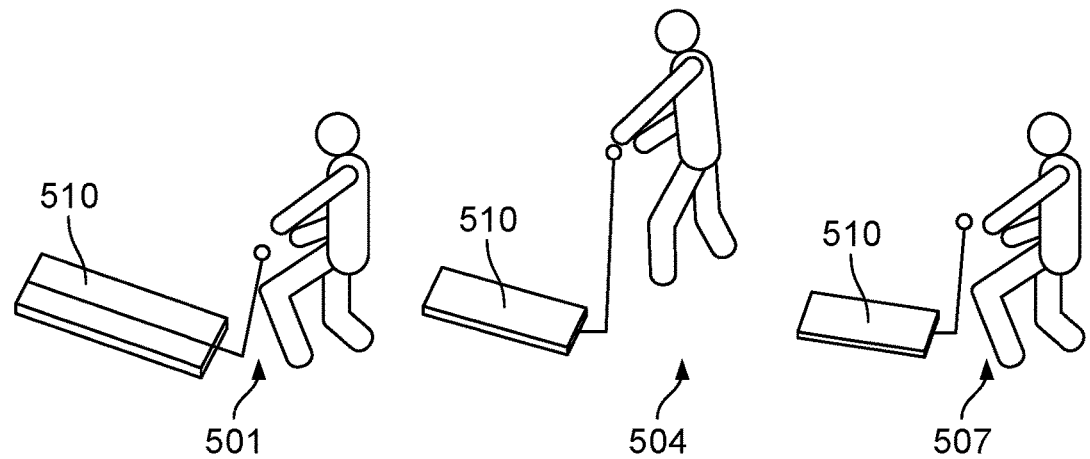
FIG. 5A is a diagram illustrating an example of an exercise.

FIG. 5A is a diagram illustrating an example of an exercise. In one embodiment, as exercise a user pulls against a cable routed through an extension arm (510) of the exercise machine. User position (501) illustrates a user in a squat position ready to begin an upward thrust. At user position (504) the user has reached the full extension. Following, the user returns back into the squat position at user position (507). In one embodiment, alteration of the visual segments is achieved by slowing the playback rate so that the user's actions are better aligned.

As a user tires, the rate at which the exercise may be continued declines and so the time between these three exemplary states, squat (501)—extended (504)—squat (507), increases. Simply slowing down the playback rate of the video may reduce the exercise cadence, but the synchronization with the user's motion is likely to be poor. This is because the actual movement portion from (501) to (504) and from (504) to (507) may remain relatively close in speed to that achieved earlier, with pauses being generated by the user at the stationary points as they catch their breath and/or physically recover.

Figure 5B:
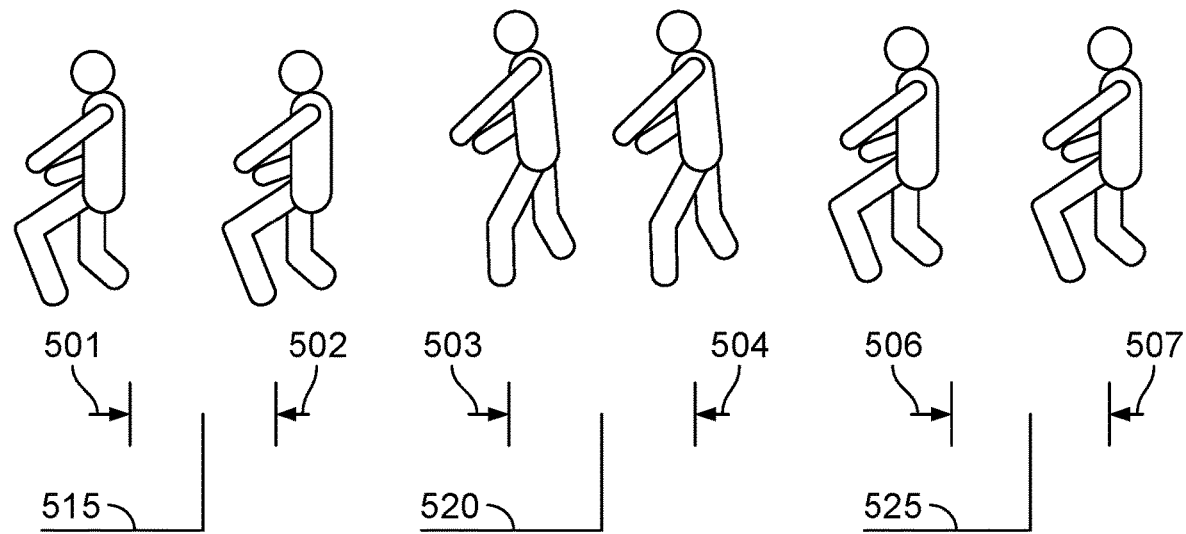
FIG. 5B is a diagram illustrating an alternate example of the exercise in FIG. 5A.

FIG. 5B is a diagram illustrating an alternate example of the exercise in FIG. 5A. In one embodiment, a brief pause is allowed, inserted as shown in FIG. 5B at the point where a movement is reversed, temporarily passing through a zero movement period. Here, the frame at the squat position (501) may be either paused for a brief time (515) wherein the visual motion continues at position (502), or the visual content local to this minimum movement segment is simply slowed to give the desired delay time (515). This solution of creating delay in playback at a minimum of movement is an improvement as the user's perception of freeze frame activity is significantly reduced when in a period that activity is minimal. Similarly, as the user approaches the extended position (503) the system delays by a time (520) to position (504) wherein a user relaxes to the squat position (506) and the system introduces delay (525) before resuming at position (507).

By contrast with periods of rapid movement where any delays introduced produce the appearance of jerky motion such as when a moving scene is illuminated with a stroboscope, a user may be less distracted by brief pauses synchronized to points of reversal. Using this technique, delays of several hundreds of milliseconds may be absorbed which corresponds well to the natural delays that occur as a user tires during an exercise sequence. If longer delays are required, a visual segment with a different actual cadence may be used with facility to change from one visual segment with one cadence to another visual segment with another cadence, such that it is hardly perceptible to an exercising user.

In one embodiment, the video element is replaced by cutting away temporarily to a different scene and then cutting back to the replacement video segment operating at a different cadence. Such a different scene can, for example, be informational such as showing a stick figure representation of postural information encouraging the user not to slouch or favor one articulation over another. Introducing commentary that recognizes a variety of postural errors that correlate with the reduction in exercise performance may be drawn from a database of exercise statistical information collected from a wide sampling of exercise machines that are already connected.

The creation of a variable timeline which departs from a fixed, predetermined schedule to accommodate a user's tendency to vary the cadence over the normal duration of an exercise is referred herein as "time-flex". This concept is also directly applicable to the desire of a user to make alterations to the exercise schedule while the exercise is in progress; for example if a user is feeling energetic, the addition of one or more additional reps may require the insertion of a matching one or more visual sequences, coupled with a change of auditory segments so that the user is encouraged to greater effort.

These insertions may be performed so as to add to the visual sequences and may not necessarily be simply a repeat of a previous segment. In one embodiment, the user is supported by being shown a more developed exerciser(s) to convey the image of an advanced performance exhibiting the characteristics of better stamina/technique. The auditory cues may also be differentiated to emphasize aspects of the exercise such as better breathing control or more even application of exercise forces.

Trigger Loops and Triggered Actions. A "trigger loop" is used by the controller (204) of FIG. 2 to loop visual and/or auditory content based on context. One example of a trigger loop is during a setup, for example setup event (310) in FIG. 3, where a user (220) needs to set up a machine in a different configuration for an exercise, say rotate part of the machine (202) to prepare it for bench press. While the machine is looking for a context trigger, in this case from sensor (210) to see whether the machine part has been rotated, visual and/or auditory content is looped. Similarly, actions involving playback of visual and/or auditory content on display (206) may be triggered from a context trigger.

Reverse Time-Flex. Time-flex may be used to keep looping visual and/or auditory content until an end of a set. In one embodiment, time-flex includes starting media content for an exercise movement and forming two program loops. In an outer program loop, the next group of media content is played. In an inner program loop within the outer program loop, for each of the group of media clips being played, it is determined whether the user is done. If no, control remains in the inner loop, and if yes, the inner loop is broken out of if the user moves on to another movement with a corresponding group of clips, or the inner and outer loops are broken out of if the user is done. In this way, the media sequences may be flexible and customized in time to a specific user, depending on if they are slower or faster. A "reverse time-flex" is used to have a content, for example auditory content, not start until a user begins a set. In the case of a reverse time-flex, the content waits for the user to start.

Figure 6A:
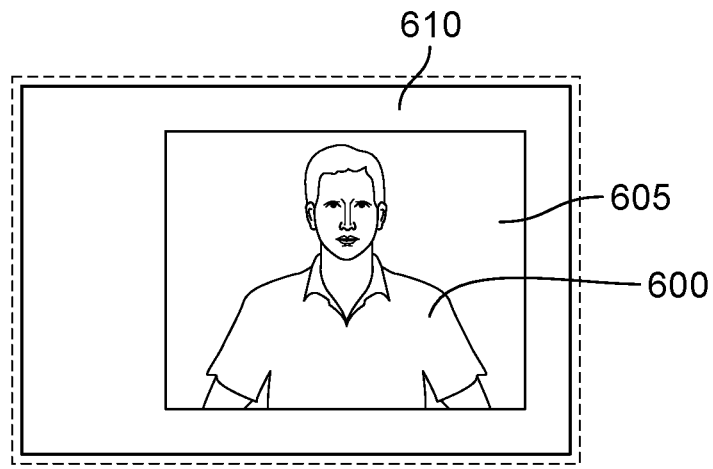
FIG. 6A is diagram illustrating an example of a foreground visual in an embodiment of a system for controlling a workout, for example that shown in FIG. 2.

FIG. 6A is a diagram illustrating an example of a foreground visual in an embodiment of a system for controlling a workout, for example that shown in FIG. 2. When a visual segment is primarily a foreground exhibit, the user exercising is being addressed or instructed directly by a coach, whether live, virtual, animated, or computer-generated. The foreground image (605) contains the coach (600) and is presented on top of the background image (610).

This may be achieved using a "green screen" technique, where the "green" background color is replaced by the desired background so as to make it appear that the coach is present in the background scene. However, during the progress of an exercise, having a single observer presented on the screen may be perceived by some users as being undesirable or intrusive; the sensation of being watched or stared at may result in a strong emotional reaction that impedes the exercise and alternatives may be provided for a more congenial scene.

Figure 6B:
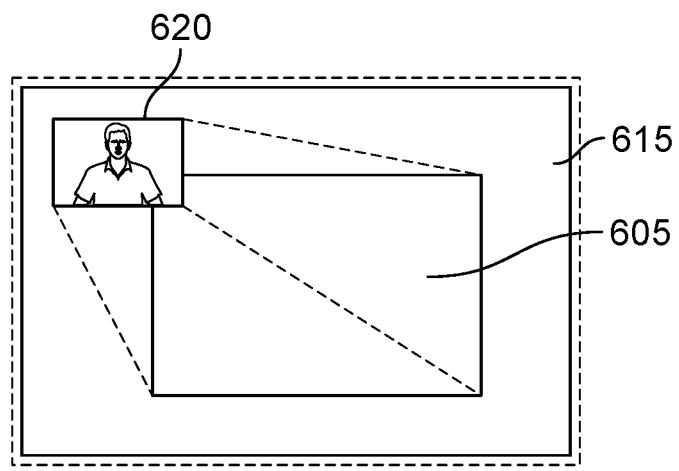
FIG. 6B is diagram illustrating an example of a replacement visual in an embodiment of a system for controlling a workout, for example that shown in FIG. 2.

FIG. 6B is diagram illustrating an example of a replacement visual in an embodiment of a system for controlling a workout, for example that shown in FIG. 2. In one embodiment, the original foreground image (605) of FIG. 6A is reduced to a smaller inset (620) and the background (615) either retained as it was at (610) or else may be used to show a different aspect of the exercise room with exercising users. The replacement scene (615) may be selected in any of a number of ways. For example, it may be pre-determined by the programming sequences that make up an exercise or exercise routine or else invoked by the user through a command option using controls that are accessible to the user.

In one embodiment, the user is prompted to indicate a background category and may select a matching exercise group of participants. In another implementation, the background is kept consistent and a coach (600) is cast to the foreground (605) for direct instruction, collapsing to a small inset (620) while the exercise continues. The inset may be brought to the foreground in response to the detection of user error during the exercise, correctional observations provided and then the inset restored to a minor position on-screen once this action is completed.

Figure 6C:
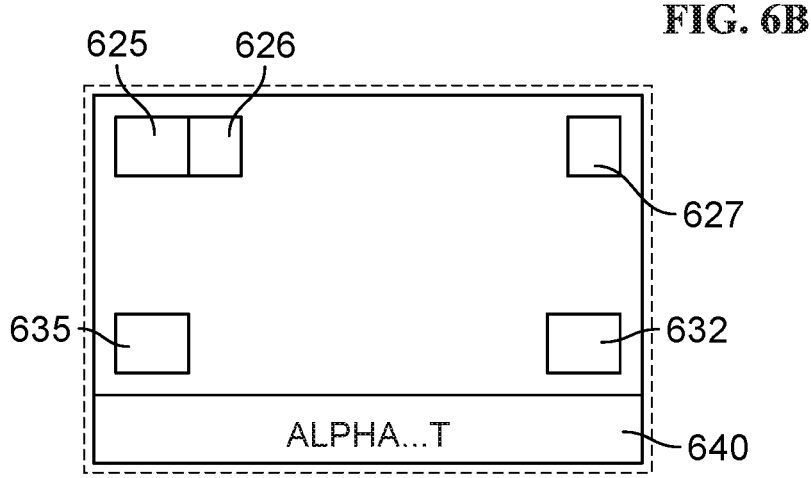
FIG. 6C is diagram illustrating an example of a correction visual in an embodiment of a system for controlling a workout, for example that shown in FIG. 2.

FIG. 6C is diagram illustrating an example of a correction visual in an embodiment of a system for controlling a workout, for example that shown in FIG. 2. As illustrated by FIG. 6C, following a correction element where the coach is brought to the foreground, the background is changed after the correctional advice is delivered and the collapsing of the foreground image of the coach moved to one of several alternative positions, (625), (627), (632) or (635) on the screen. This is an improvement that attempts to keep the user engaged and reduces boredom that may result from an unchanging visual program. The behavior of the visual controller has significant flexibility that allows each user to experience a range of engagements with the exercise machine and its coach(s). There are no implicit restrictions on the media that supports the user's exercise regime and timing of events. The duration of segments as well as the positioning of the information are freely alterable, with the caution that this should support the user's workout and not distract the user by being unpredictable.

FIG. 6C also shows the addition of text information (640) that may be used to reinforce advice and/or cue emphasis. The position is shown for this example at the base of the visual display but may be in any position on the screen. For example, subtitles and count-down information may be shown for those that are hearing impaired. In one embodiment, the accessibility displays may be positioned so as to make it easier for the hearing impaired to view both text and a signing artifact, shown here as (626) adjacent to the active inset image at (625).

Content Creation and Algorithmic Development. In one embodiment, a dashboard or other authoring tools are used to create, edit, select, and/or remove any combination of user interface (UI) elements comprising: coach, model, voice audio, music, haptic, graphics, and/or public relations halo for a given workout and/or timeline. A selector may be at least one of the following: an engineer, a non-technical creator, a user, and a third-party. A non-technical creator may use a dashboard or other authoring tool to enable a non-technical coach and/or user to build their own workout. This permits a user a continuum from a completely guided workout to a completely custom workout, and includes elements of both. For a third-party, an application programming interface (API) enables third parties to build and submit workouts for use on the machine (202) of FIG. 2.

Rewards. An essential component of a successful exercise strategy is rewarding the user for completion of meeting particular goals. The controller (204) and/or processor (208) of FIG. 2 may include using a celebration routine that provides gratifying events for the user.

In one embodiment, the reward is an auditory/musical sequence accompanied by a visual sequence displayed to the user. This is appended to the timeline to coincide with a particular predetermined goal. For example, a measure of user performance such as completion of an exercise routine within a particular time limit may invoke this celebration sequence. For hearing impaired users, the resistance/loading mechanism may provide haptic/tactile stimulation by applying a pulsating load, along with a visual sequence that celebrates achievement.

In one embodiment, the user earns bonus points which allows the selection of supplementary exercises and/or graduation to a different competitive level. This latter implementation may be applied as part of a loyalty program administered by segments of the hospitality industry in which keys for program participants may comprise the access qualification for a range of perquisites not provided for the general public. One particular benefit of an exercise machine based on a media centered controller which incorporates a dynamically alterable timeline is that a fully customized experience is practical and thus may be used to augment certain brands while retaining the same basic mechanical design and appearance.

A user may be unable to complete an exercise successfully or else may progress to completion at a slower rate than anticipated. As shown above, the controller (204) may provide a modified timeline sequence that accommodates a user's incapacity. For example, if the user experiences a stamina hurdle where the usual numbers of repetitions are not achievable or exceed the limits of a predetermined working range, then alternative video sequences may be selected to replace the standard sequences. For users with physical disabilities range of motion may be a restriction, but because the exercise machine (202) is interactive and able to measure actual performance, visual and/or auditory elements may be adjusted for the disability for the display (206).

The visual segments that appear in a timeline generally account for the performance level of the user. For example, a user may choose to set the starting value for the exercise set being used to "20% increase." The user records may then be updated to reflect these user selections. If the user typically chooses to offset the starting value for the exercises and shows no performance deterioration, then for that specific set when used again, the exercise machine may use this typical setting as a starting point.

A significant user group is the elderly or infirm that seek to improve their condition through exercise and it should be clear that if the coaching presentation is too mismatched with the expectations of the individual user then this can be seen as discouraging. Accordingly, in the same way as described for the use by a user with physical disabilities, the exercise machine (202) selects and modifies the timeline content based on user input and actual user performance as exercise proceeds.

In summary, a timeline and media controller for an exercise machine is disclosed responsive to user performance that allows the user to interact with a personal trainer or coach without having to be physically present at the same location as the coach. A dynamically alterable sequence accommodates changes to improve coaching. The controller provides appliance control synchronized to pre-determined lessons or exercise sessions that may be altered automatically and/or on-the-fly to accommodate the user's requirements by inserting and/or removing visual elements and auditory elements that make up the appliance interaction interface.

Exercise sessions may be stored in memory and/or downloaded from a remote server and these sessions comprise linked media components that give a user a flexible instructional and motivational environment within which to exercise. The controller monitors the user's exercising and selects exercise program sequences and creates the timeline that defines, adjust or modifies the base exercise program to optimize user performance.

Figure 7:
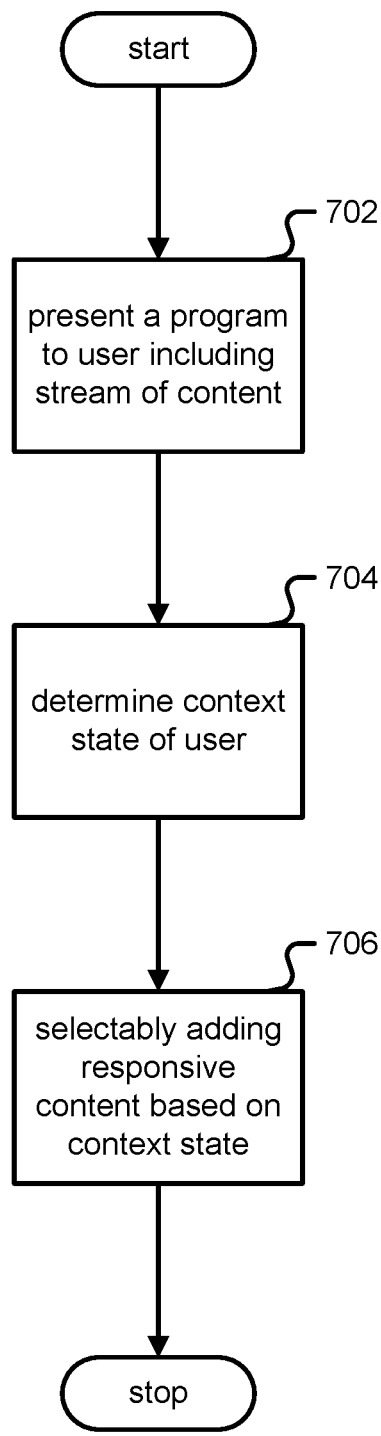
FIG. 7 is a flow diagram illustrating an embodiment of a process for timeline and/or media control of an exercise machine.

FIG. 7 is a flow diagram illustrating an embodiment of a process for timeline and/or media control of an exercise machine. In one embodiment, the controller (204) of FIG. 2 is used to carry out the process of FIG. 7.

In step (702), a program is presented to a user including a stream of content including a first auditory content and a first visual content related to the workout.

In step (704), a context state of the user participating in the workout is determined based on information from a sensor. The context state of the user may be different than an initial state of the user that the first auditory content or the first visual content is based on.

In step (706), responsive content based on the context state of the user is selectably added to the stream of content in a manner to reduce or avoid conflict between the stream of content and the responsive content. The responsive content may be personalized content based on the context state of the user. Avoiding or reducing conflict means preventing the responsive content from interrupting, colliding, or being introduced in a manner that provides a disjointed user experience. For example, the responsive content may delay the currently playing audible content and be inserted at a reasonable break during the currently playing content. In the case of an urgent message, the currently playing audible content may be stopped and resumed or the responsive content may play over the currently playing content. Similarly, the responsive content may delay the currently playing visual content and be inserted at a reasonable break. In cases of an urgent event, the original playing visual content may be re-inserted over the currently playing responsive visual content.

In one embodiment, the context state of the user is a personalized identifier. In one embodiment, the context state of the user is based at least in part on a function of a historical/past exercise. In one embodiment, the context state of the user is based at least in part on a function of a future exercise. In one embodiment, the responsive content is non-repetitive content based on the context state of the user, wherein the context state of the user comprises a record of historical/past content.

In one embodiment, the responsive content comprises coaching from a second coach, wherein the first auditory content or the first visual content is based on a first coach. In one embodiment, the responsive content comprises content comprising at least one of iconography and text. In one embodiment, the responsive content comprises a text content, and wherein the processor is further configured to process the text content into speech using a text-to-speech engine.

In one embodiment, the responsive content comprises one or more of the following: a form feedback content; a trigger loop; a time-flex loop; a reverse time-flex loop; a machine setup feedback content; and a selection based on mood. As referred to herein, "form feedback" is a way to communicate/coach better form/posture for a given movement, for example to have a straight back during a specific weight press movement.

Figure 8:
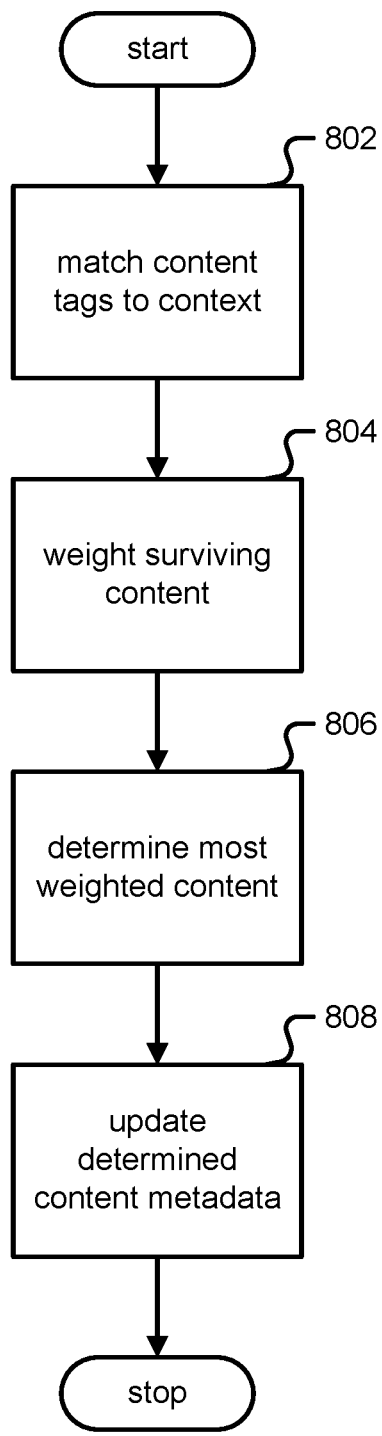
FIG. 8 is a flow diagram illustrating an embodiment of a process for responsive content determination.

FIG. 8 is a flow diagram illustrating an embodiment of a process for responsive content determination. In one embodiment, the process of FIG. 8 is part of step (706) of FIG. 7.

In step (802), the controller (204) may run a set of functions against content to determine the responsive content to play. In one embodiment, the context state of the user is matched against a set of metadata for content, such as the set described herein in Table 1. In one embodiment, context may be algorithmic in the sense that formula may be used to curate content associated with presecribedReps>=3 AND weightOn==TRUE.

In step (804), the content that survives past step (802) is weighted based on tags for surviving content in comparison to various aspects of the context state. For example, if the current movement context state is "bench press", then any content applicable to that movement that includes it on their <movement> tag would have an increase of +5 on their weight. Likewise, if the context state needs coaching on the right side of a movement, any content with a <side> tag of "right" would have an increase of +1 on their weight.

In step (806), the controller (204) determines the most weighted content to inject into the timeline as responsive content. In the event there are more than one candidates, the controller (204) may elect to choose randomly or in another way.

In step (808), the controller (204) updates metadata for the determined content in step (806). That is, a lastPlayed tag may be updated to indicate the content was played at 09:25 UTC, to reduce the chance the same content is played again in the near future.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system for controlling a workout, comprising:
a sensor;
a processor coupled to the sensor, wherein the processor is configured to determine a context state of a user participating in the workout based on information from the sensor; and
a media controller coupled to the processor, wherein the media controller is configured to present a program to the user including a stream of content including a first auditory content and a first visual content related to the workout;
wherein the processor causes a responsive content based on the context state of the user to be selectably added to the stream of content in a manner that avoids conflict with the stream of content, wherein the responsive content is selectably added to adjust a cadence of the workout, and wherein the cadence of the workout is adjusted at least in part by inserting the responsive content to extend a silent period.

2. The system of claim 1, wherein avoiding conflict with the stream of content comprises avoiding conflict with the first auditory content.

3. The system of claim 1, wherein avoiding conflict with the stream of content comprises avoiding conflict with the first visual content.

4. The system of claim 1, wherein for the responsive content based on the context state of the user, the context state of the user is different than an initial state of the user that the first auditory content or the first visual content is based on.

5. The system of claim 1, wherein the responsive content is personalized content based on the context state of the user, wherein the context state of the user comprises a personalized identifier.

6. The system of claim 1, wherein the context state of the user is based at least in part on a function of a historical exercise.

7. The system of claim 1, wherein the context state of the user is based at least in part on a function of a future exercise.

8. The system of claim 1, wherein the responsive content is non-repetitive content based on the context state of the user, wherein the context state of the user comprises a record of past content.

9. The system of claim 1, wherein the responsive content comprises coaching from a second coach, wherein the first auditory content or the first visual content is based on a first coach.

10. The system of claim 1, wherein the processor is further configured to run a set of functions against content to determine the responsive content to play.

11. The system of claim 1, wherein the processor is further configured to match the context state of the user against a set of metadata for content.

12. The system of claim 1, wherein the responsive content comprises content comprising at least one of iconography and text.

13. The system of claim 1, wherein the responsive content comprises a text content, and wherein the processor is further configured to process the text content into speech using a text-to-speech engine.

14. The system of claim 1, wherein the responsive content comprises a form feedback content.

15. The system of claim 1, wherein the responsive content comprises a trigger loop.

16. The system of claim 1, wherein the responsive content comprises a time-flex loop.

17. The system of claim 1, wherein the responsive content comprises a reverse time-flex loop.

18. The system of claim 1, wherein the responsive content comprises a machine setup feedback content.

19. The system of claim 1, wherein the responsive content comprises a selection based on mood.

20. The system of claim 1, wherein the sensor comprises at least one of the following: a power switch, a database query, a camera, a depth sensing camera, a seat sensor, a push force sensor for a user foot, a pull force sensor for a user foot, a seat to rail position sensor, and a handle sensor.

21. The system recited in claim 1, wherein the responsive content comprises a filler utterance.

22. The system recited in claim 1, wherein the first auditory content and the first visual content comprise separate portions of the stream of content.

23. The system recited in claim 22, wherein the first auditory content comprises an auditory stream comprising a plurality of auditory elements, and wherein the responsive content is inserted between auditory elements.

24. The system recited in claim 1, wherein the responsive content is selected from a plurality of candidate responsive content.

25. The system recited in claim 1, wherein the responsive content is selected from the plurality of candidate responsive content based at least in part on weighting of the candidate responsive content, and wherein the weighting of the candidate responsive content is based at least in part on the context state of the user.

26. A method for controlling a workout, comprising:
presenting a program to a user including a stream of content including a first auditory content and a first visual content related to the workout;
determining a context state of the user participating in the workout based on information from a sensor; and
selectably adding a responsive content based on the context state of the user to the stream of content in a manner that avoids conflict with the stream of content, wherein the responsive content is selectably added to adjust a cadence of the workout, and wherein the cadence of the workout is adjusted at least in part by inserting the responsive content to extend a silent period.

27. A computer program product embodied in a non-transitory computer readable medium and comprising computer instructions for:
presenting a program to a user including a stream of content including a first auditory content and a first visual content related to the workout;
determining a context state of the user participating in the workout based on information from a sensor; and
selectably adding a responsive content based on the context state of the user to the stream of content such that the stream of content and the responsive content do not conflict, wherein the responsive content is selectably added to adjust a cadence of the workout, and wherein the cadence of the workout is adjusted at least in part by inserting the responsive content to extend a silent period.

* * * * *